US008043832B2

(12) United States Patent
Miyoshi et al.

(10) Patent No.: US 8,043,832 B2
(45) Date of Patent: Oct. 25, 2011

(54) METHOD FOR DETERMINATION OF INFLAMMATORY BOWEL DISEASE

(75) Inventors: Eiji Miyoshi, Suita (JP); Hideki Iijima, Suita (JP); Shinichiro Shinzaki, Suita (JP); Masahiko Tsujii, Suita (JP); Norio Hayashi, Suita (JP); Takatoshi Nakagawa, Suita (JP); Akihiro Kondo, Suita (JP); Naoyuki Taniguchi, Suita (JP)

(73) Assignee: Osaka University, Suita-shi, Osaka (JP)

( * ) Notice: Subject to any disclaimer, the term of this patent is extended or adjusted under 35 U.S.C. 154(b) by 317 days.

(21) Appl. No.: 12/301,294

(22) PCT Filed: May 18, 2007

(86) PCT No.: PCT/JP2007/060257
§ 371 (c)(1),
(2), (4) Date: Nov. 18, 2008

(87) PCT Pub. No.: WO2007/136001
PCT Pub. Date: Nov. 29, 2007

(65) Prior Publication Data
US 2009/0186371 A1    Jul. 23, 2009

(30) Foreign Application Priority Data

May 19, 2006    (JP) ................................. 2006-140457

(51) Int. Cl.
*C12P 21/04* (2006.01)
(52) U.S. Cl. ...................................................... 435/69.6
(58) Field of Classification Search .................. 435/69.6
See application file for complete search history.

(56) References Cited

U.S. PATENT DOCUMENTS

| | | | |
|---|---|---|---|
| 6,777,197 | B1 | 8/2004 | Shimoyama et al. |
| 2005/0074818 | A1 | 4/2005 | Bergmann et al. |

FOREIGN PATENT DOCUMENTS

| | | |
|---|---|---|
| EP | 0 698 793 A2 | 2/1996 |
| EP | 0 756 173 A1 | 1/1997 |
| JP | 07-209301 | 8/1995 |
| JP | 08-82623 | 3/1996 |
| JP | 08-220099 | 8/1996 |
| JP | 2005-504321 | 2/2005 |
| WO | WO 99/34218 | 7/1999 |
| WO | WO 03/029824 A1 | 4/2003 |
| WO | WO 2005/054853 A3 | 6/2005 |

OTHER PUBLICATIONS

Bond et al. "A detailed lectin analysis of IgG glycosylation, demonstrating disease specific changes in terminal galactose and N-acetylglucosamine", J of Autoimmunity, 1997, 10:77-85.*
Alavi et al. "The pivotal nature of sugars in normal physiology and disease", WMW, 2006, 156(1-2):19-33.*
Kuroda, et al., "Structural Studies on IgG Oligosaccharides of Patients with Primary Sjögren's Syndrome", Glycoconjugate Journal, vol. 19, No. 1, Jan. 2002, pp. 23-31.
Masuda, et al., "Pairing of Oligosaccharides in the Fc Region of Immunoglobulin G", FEBS Letters, vol. 473, No. 3, May 19, 2000, pp. 349-357.
Parekh et al., "A Comparative Analysis of Disease-Associated Changes in the Galactosylation of Serum IgG", Journal of Autoimmunity, vol. 2, No. 2, Apr. 1, 1989, pp. 101-114.
Tsuchiya, et al., "Detection of Glycosylation Abnormality in Rheumatoid IgG using N-Acetylglucosamine-Specific Psathyrella Velutina Lectin" The Journal of Immunology, vol. 151, No. 2, Jul. 15, 1993, pp. 1137-1146.
Supplementary European Search Report for PCT/JP2007/060257 Dated Nov. 3, 2009.
Written Opinion of the International Searching Authority, Application No. PCT/JP2007/060257, mailed Jul. 24, 2007 (English Translation).
Thomas W. Rademacher et al., "The Role of IgG Glycoforms in the Pathogenesis of Rheumatoid Arthritis", Springer Seminar Immunopathology, 1988, pp. 231-249, vol. 10.
R Dubé et al., "Agalactosy IgG in Inflammatory bowel disease: Correlation with C-Reactive Protein", Gut, 1990, pp. 431-434, vol. 31.
Mae F. Go et al., "Deficient Galactosylation of Serum IgG in Inflammatory Bowel Disease: Correlation with Disease Activity", J. Clin Gastroenterol, 1994, pp. 86-87, vol. 18(1).
Takara Bio Online Catalogue, Method for Analyzing Human IgG Oligosaccharides using Palstation, http://bio.takara.co.jp/catalog/catalog_d.asp?C_ID=C0730, Mar. 15, 2006, pp. 1-6 (with full English Translation).
Picolumi® CA RF, "A Diagnosing kit for the Determination Serum Anti-Agalactosy IgG Anitbodies", pp. 1-20 (with full English translation). Feb. 2005.

* cited by examiner

*Primary Examiner* — Sue Liu
*Assistant Examiner* — Bin Shen
(74) *Attorney, Agent, or Firm* — Nixon Peabody LLP; Jeffrey L. Costellia

(57) ABSTRACT

The instant invention provides a method for the differential diagnosis of inflammatory bowel disease which comprises, determining the relative ratio of G0 oligosaccharide represented by formula (I):

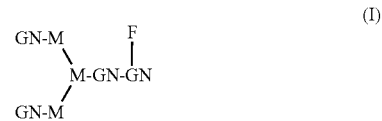

to G2 oligosaccharide represented by formula (II):

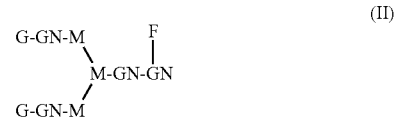

wherein G represents galactose, M represents mannose, GN represents N-acetylglucosamine and F represents fucose in serum IgG oligosaccharide fraction obtained from a patient with inflammatory bowel disease or a patient with suspicion of inflammatory bowel disease, and
discriminating inflammatory bowel disease based on the obtained ratio.

3 Claims, 11 Drawing Sheets

--Prior Art--

--Prior Art--

METHOD FOR DETERMINATION OF INFLAMMATORY BOWEL DISEASE

TECHNICAL FIELD

The instant invention relates to a method for the differential diagnosis of inflammatory bowel disease. In more detail, the instant invention relates to a method for the differential diagnosis between ulcerative colitis and Crohn's disease in a patient with inflammatory bowel disease.

BACKGROUND ART

Inflammatory bowel disease (IBD), including Crohn's disease (CD) and ulcerative colitis (UC), is one of intractable diseases and there are about 120 thousands patients with IBD in Japan. Nowadays, differential diagnosis between ulcerative colitis and Crohn's disease in a patient with IBD is mainly conducted by pathological features including specific appearance observed by barium enema, endoscope observation, presence or absence of epithelioid cell granuloma as well as clinical features including presence or absence of blood in stool and perianal lesions. Those criteria require endoscopy which invites large burden on the patient being diagnosed. A noninvasive and objective method for differential diagnosis of a patient with inflammatory bowel disease has been desired.

Immunoglobulin G (hereinafter, IgG) is a glycoprotein and is constituting about 75-85% of serum immunoglobulins in normal humans. As shown in FIG. 1, IgG is a symmetric molecule built of two identical H chains and two identical L chains.

IgG carries oligosaccharides in their Fc fragment and the oligosaccharide plays an important role in keeping the steric structure of IgG. In addition, the oligosaccharide affects the interaction between IgG and Fcγ receptor or effecter molecules such as complement. Sixteen IgG oligosaccharides shown in FIG. 2 have been known.

In healthy people, the relative rates among the 16 IgG oligosaccharides are approximately constant. However, the oligosaccharide balance is specific in patients with myeloma or rheumatoid arthritis (RA). For example, patients with rheumatoid arthritis have significantly increased levels of serum agalactosyl immunoglobulin G (IgG) which lacks terminal galactose in the IgG oligosaccharide. A method for diagnosing RA based on this finding has been proposed (non-patent literature 1) and methods for determining relative ratio of oligosaccharides (Patent Literature 1) and for detecting anti-agalactosyl IgG autoantibodies (CARF) in the sera (non-patent literature 2) have been developed. Although CARF correlates with disease activity of RA, it has been revealed that CARF does not necessarily reflect the amount of serum agalactsyl IgG.

Diagnosis based on IgG oligosaccharide alteration has been proposed for diagnosing AIDS condition (patent literature 2), hepatic diseases, malignant hypertension, immunoglobulin A nephropathy and diseases in children (patent literature 3). Especially, the increase of serum agalactosyl IgG has been reported in patients with inflammatory diseases (Non patent literature 3) and among the inflammatory diseases, the increase of serum agalactosyl IgG is significant in patients with autoimmune diseases. Acute phase cytokines such as TNF and IL6 have been suggested to play a role in the mechanism for the increase of agalactosyl IgG in a patient with such disease as above. However, the detail has not yet been revealed. It has been reported that agalactosyl IgG in the sera of patients with inflammatory bowel disease including Crohn's disease and ulcerative colitis is higher than that in the sera of healthy people. It has also been suggested that the amount of serum agalactosyl IgG correlates with C-reactive protein (CEP) and clinical activity (Non patent literatures 4 and 5). However, these reports were made on the ratio of agalactsyl IgG oligosaccharide in all serum IgG oligosaccharide fractions. No study has yet been reported on the correlation of the relationship between specific IgG oligosaccharides and IBD.

[Patent Literature 1] JP 8-220099 A
[Patent Literature 2] JP 7-209301 A
[Patent Literature 3] JP 8-82623 A
[Non Patent Literature 1] TAKARA BIO ONLINE CATALOGUE "Method for analyzing human IgG oligosaccharides using PALSTATION®" bio.takara.co.jp/catalog/catalog d.asp?C ID=C0730, searched and downloaded on Mar. 15, 2006.
[Non Patent Literature 2] Package insert of PICOLUMI® CA•RF, a diagnosing kit for the determination serum anti-agalactosy IgG antibodies
[Non Patent Literature 3] Thomas W. Rademacher et al., Springer Semin Immunopathol, Vol. 10, 231-249 (1998)
[Non Patent Literature 4] R Dube et al., Gut, Vol. 31, 431-434 (1990)
[Non Patent Literature 5] Mae F. G0 et al., J. Clin. Gastroenterol. Vol. 18, 86-87 (1994)

DISCLOSURE OF THE INVENTION

Problem(s) to be Solved by the Invention

An object of the invention is to provide an objective and non-invasive method for the differential diagnosis of inflammatory bowel disease.

Means to Solve the Problem(s)

The invention provides a method for the differential diagnosis of inflammatory bowel disease which comprises; determining the relative ratio of G0 oligosaccharide shown by formula (I):

to G2 oligosaccharide shown by formula (II):

wherein G represents galactose, M represents mannose, GN represents N-acetylglucosamine and F represents fucose in serum IgG oligosaccharide fraction obtained from a patient with inflammatory bowel disease or a patient with suspicion of inflammatory bowel disease, and discriminating inflammatory bowel disease based on the obtained ratio.

According to the method of the instant invention, the ratio of the amount of G0 oligosaccharide represented by formula (I) to the amount of G2 oligosaccharide represented by formula (II) (G0/G2) is determined. When the ratio is higher than a predetermined value, the patient is diagnosed as Crohn's disease, whereas when the ratio is lower than a predetermined value, the patient is diagnosed as ulcerative colitis.

Effect of the Invention

According to the instant invention, differential diagnosis between ulcerative colitis and Crohn's disease in a patient with inflammatory bowel disease or a patient with suspicion of inflammatory bowel disease become possible. The method of the instant application uses peripheral blood obtained from the patient and therefore, causes less burden on the patient than the conventional differential diagnosis which requires endoscopic observation.

In more particularly, the method of the invention can determine whether a patient with inflammatory bowel disease has ulcerative colitis or Crohn's disease. In the conventional differential diagnosis between ulcerative colitis and Crohn's disease, the diagnosis has been conducted in a comprehensive manner based on barium-enema findings, endoscopic appearance, histological findings including presence or absence of epitheloid granulomas in addition to the presence or absence of blood in stool and perianal lesion. According to the present invention, the differential diagnosis between ulcerative colitis and Crohn's disease in a patient with inflammatory bowel disease can be conducted using peripheral blood obtained from the patient who has been diagnosed as inflammatory bowel disease by non-invasive clinical observations such as presence or absence of blood in stool and perianal lesion. The method of the instant invention can significantly relieve the mental and physical burden on the patient caused by the conventional differential diagnosis. In addition, G0/G2 ratio used in the present invention is also useful as a marker for prognostication in patients with inflammatory bowel disease.

BEST MODE FOR CARRYING OUT THE INSTANT INVENTION

Figure 1:
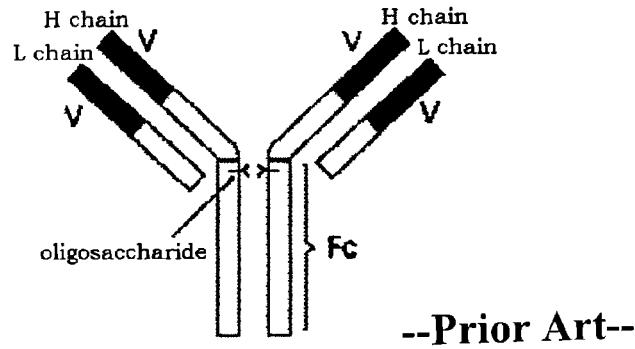
FIG. 1 Schematic structure of IgG antibody.

According to the method of the present invention, serum derived from peripheral blood of the patient is used. In the specification and claims of the instant application, "patient with inflammatory bowel disease" or "patient with suspicion of inflammatory bowel disease" refers a patient who has already been diagnosed as inflammatory bowel disease based on conventional clinical criteria for inflammatory bowel disease or a patient with clinical suspicion of inflammatory bowel disease based on conventional clinical criteria for inflammatory bowel disease.

According to the method of the present invention, the structures of the IgG oligosaccharides in the serum derived from the patient's peripheral blood are examined. Serum of the patient may be derived from the peripheral blood by any procedure used in clinical examinations.

IgG is purified from the serum and the oligosaccharides attached to the IgG are analyzed. As is disclosed in Non-Patent Literatures 1 and 3, several procedures to analyze the IgG oligosaccharide profile have been known. In the method of the present invention, any procedure may be employed so long as it can determine the relative ratio of G0 oligosaccharide represented by formula (I) to G2 oligosaccharide represented by formula (II) in serum IgG oligosaccharides. For example, a procedure which comprises the steps of: isolating and labeling the oligosaccharides and analyzing them with HPLC to determine the relative ratio of G0 oligosaccharide to G2 oligosaccharide, may be employed.

In one embodiment, the method of the present invention comprises the steps of:
1) isolating immunoglobulin G from the serum of a patient with inflammatory bowel disease,
2) releasing oligosaccharides from the immunoglobulin G,
3) measuring the relative ratio between G2 oligosaccharide and G0 oligosaccharide, and
4) discriminating inflammatory bowel disease based on the obtained ratio.

Each step of the method can be conducted by any known procedure. For example, the IgG oligosaccharide profile of a patient may be obtained by isolating IgG from the serum using protein A, releasing oligosaccharides from the IgG using N-glycanaze, labeling the oligosaccharides with fluorescence and analyzing the labeled oligosaccharides by HPLC to give the profile.

This embodiment will be described in more detail. Protein A binds specifically to IgG. Columns packed with a carrier to which protein A is attached are available on the market and IgG may be isolated by loading the serum onto said column.

The oligosaccharides are released from the isolated IgG. The release of the oligosaccharides may be carried out by means of chemical procedures such as hydrazinolysis and N-acetylation, or enzymatic procedures using an enzyme such as N-glycanase. Any of those procedures can be employed in the instant method. The oligosaccharides released from IgG are then treated to give pyridylamino (PA)-oligosaccharide. The PA-oligosaccharides are subjected to HPLC analysis using a commercially available column for oligosaccharide analysis according to the manufacturer's protocol.

Figure 2:
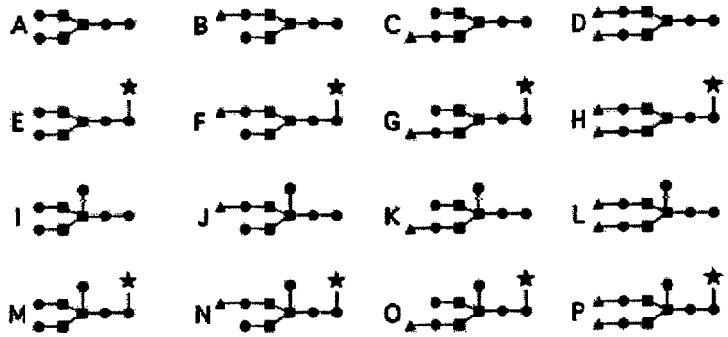
FIG. 2 Structures of 16 oligosaccharides attached to IgG.
Figure 3:
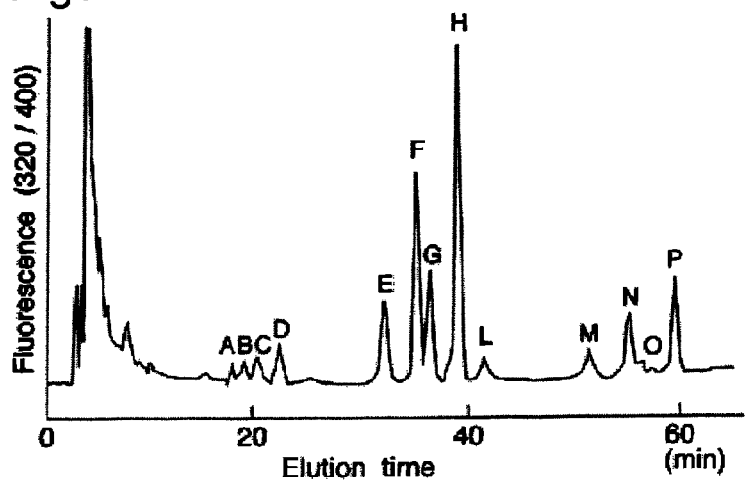
FIG. 3 Correspondence between HPLC peaks and oligosaccharides shown in FIG. 2.
Figure 4:
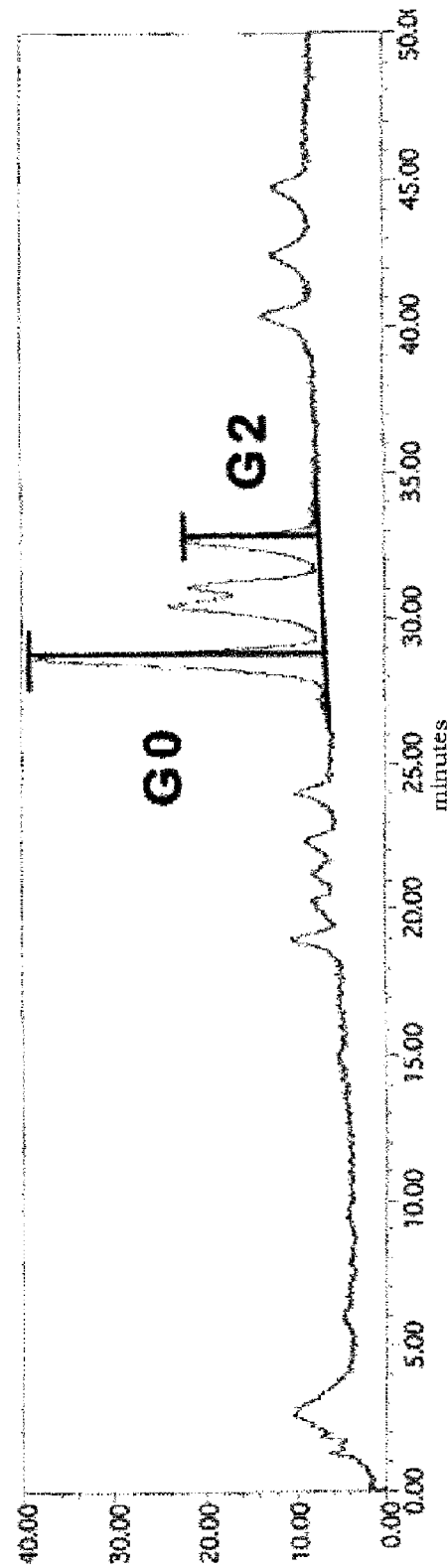
FIG. 4 Determination of G0/G2 based on HPLC profile.

HPLC profile of IgG oligosaccharides is shown in FIG. 3. In FIG. 3, peaks corresponding to the respective oligosaccharides shown in FIG. 2 are indicated with the same alphabets as FIG. 2. The basic concept for determining G0/G2 is shown in FIG. 4. In this embodiment, peak height ratio of G0 oligosaccharide to G2 oligosaccharide is used as the relative amount of G0 oligosaccharide to G2 oligosaccharide.

In another embodiment of the present invention, anti-IgG (G0 oligosaccharide) antibody and anti-IgG (G2 oligosaccharide) antibody may be prepared and the IgG oligosaccharide profile in the serum of the patient may be determined using those antibodies by means of a conventional method such as ELISA. The antibodies may be polyclonal or monoclonal so long as they can discriminate IgG (G0 oligosaccharide) and IgG (G2 oligosaccharide) and determine their relative amount. Procedures for the preparation of antibodies as well as for conducting ELISA have been well known to the art and any of those known methods can be employed.

According to the present invention, the differential diagnosis in a patient with inflammatory bowel disease is conducted based on thus obtained ratio of G0 oligosaccharide to G2 oligosaccharide in the serum obtained from the patient. When the ratio of G0 to G2 (G0/G2) is higher than a predetermined value, the patient is diagnosed as having Crohn's disease or as having suspicion of Crohn's disease. When the ratio of G0 to G2 (G0/G2) is lower than a predetermined value, the patient is diagnosed as having ulcerative colitis or as having suspicion of ulcerative colitis.

Further, the higher G0/G2 ratio in a patient means the higher severity of the inflammatory bowel disease in the patient or the higher severity is expected in the future.

In this context, "predetermined value" will be determined after the protocol for measuring the IgG oligosaccharide profile is fixed. The value is set based on the G0/G2 ratios in the serum obtained from patients who were already distinguished as having Crohn's disease or ulcerative colitis based on the conventional differentiate criteria and those in the serum obtained from healthy volunteers by the fixed protocol.

For example, in the method described in the working example of the instant specification in which the IgG oligosaccharides are isolated from IgG and the relative amount of G0 oligosaccharide to G2 oligosaccharide (G0/G2) is determined as ratio of the HPLC peak heights corresponding to the respective oligosaccharides, an inflammatory bowel disease patient with a G0/G2 equal to or higher than 1.5, preferably, equal to or higher than 2.0 and especially, equal to or higher than 2.1 will be diagnosed as having Crohn's disease or having suspicious of Crohn's disease. On the other hand, an inflammatory bowel disease patient with a G0/G2 lower than 2.1, preferably lower than 2.0 and more preferably, lower than 1.5 will be diagnosed as having ulcerative colitis or having suspicious of ulcerative colitis. This value is not limited and more reliable value will be obtained by the practicians with the accumulation of data obtained according to the same protocol from increased number of patients.

It has been known that patients with rheumatoid arthritis have significantly increased levels of serum agalactosyl IgG. It has also been known that patients with other inflammatory disease have altered IgG oligosaccharide profiles. Therefore, upon conducting the differential diagnosis in a patient with inflammatory bowel disease by the present invention, the accompanying diseases should be considered.

In another embodiment of the present invention, when G0/G2 ratio in an inflammatory bowel disease patient is lower than a predetermined value, the prognosis of inflammatory bowel disease is predicted good. In this embodiment, the "predetermined value" will be determined based on G0/G2 ratio in the serum obtained from the healthy volunteers. For example, the predetermined value may be the average ±2SD of G0/G2 ratios in the sera derived from healthy volunteers. One example of the value in this embodiment is 1.4. However, as is discussed above, this value is not limited.

The kit of the present invention for conducting the method of the invention comprises agents for measuring the amounts of G0 and G2 oligosaccharides. As discussed above, the amounts of G0 and G2 oligosaccharides in the serum of a patient can be measured by HPLC or by ELISA using anti-IgG (G0-oligosaccharide) antibody and anti-IgG (G2-oligosaccharide) antibody. Accordingly, "agents for determining the amounts of G0 and G2 oligosaccharides in the serum" may include any agent used for the measurement protocol.

One embodiment of the kit may include (1) an agent for isolating IgG in the serum; and (2) an agent for releasing the oligosaccharides from the IgG. The agent for isolating IgG in the serum may be any agent used in known procedures for this purpose and may include column containing protein-A or protein-G. The kit of this embodiment may further comprise an agent for modifying the released oligosaccharides such as 2-aminopyridine and/or a HPLC column for analyzing oligosaccharides.

In another embodiment, the kit may be that adopted for the ELISA method and comprise (1) anti-IgG (G0-oligosaccharide) antibody; (2) anti-IgG (G2-oligosaccharide) antibody; (3) solid support for immobilizing IgG (G0-oligosaccharide) and IgG (G2-oligosaccharide) thereon, for example, microplate, plastic tube or beads; and (4) an enzyme for the detection, such as horseradish peroxidase or alkaline phosphatase and the substrate for the enzyme. The kit of the present invention may further comprise an appropriate diluent, washing agent, and the standard agents.

In this study, the inventors have revealed that the β-1,4-galactosyltransferase 1 (β4GalT 1) mRNA expression is increased in ulcerative colitis patients and significantly higher β4GalT 1 activity is observed in ulcerative colitis patients than those in Crohn's disease patients or healthy controls (Example 6). Accordingly, the instant application encompass the method for the differential diagnosis of inflammatory bowel disease which comprises measuring the activity of β-1,4-galactosyltransferase in a patient with inflammatory bowel disease or a patient with suspicion of inflammatory bowel disease, and discriminating inflammatory bowel disease based on the result of the measurement.

EXAMPLES

Example 1

Serum samples were collected from peripheral blood of the people shown in Table 1 by the conventional manner: 27 patients with Crohn's disease (CD), 27 patients with ulcerative colitis (UC) and 10 healthy controls (HC). No patient was suffered from rheumatoid arthritis.

TABLE 1

PATIENTS BACKGROUNDS

|  | CD | UC | HC |
|---|---|---|---|
| number | 27 | 27 | 10 |
| (male/female) | (22/5) | (16/11) | (6/4) |
| age | 39 ± 16 | 40 ± 16 | 37 ± 12 |
| CRP | 2.1 ± 4 | 1.7 ± 4 | — |

Serum IgG was purified using ImmunoPure IgG Purification Kit (Takara Bio Inc.) according to the manufacturer's protocol.

The obtained IgG fraction in an amount of about 2 nmol was put in a microcentrifuge tube and lyophilized. $NH_4HCO_3$ (pH 8.6) 40 µl and water 20 µl were added to the tube and dissolve the content. Glycopeptidase F (Takara Bio Inc.) 20 µl (10 mU) was added to the tube and the tube was incubated overnight at 37° C. The tube was added with 100 mM ammonium acetate (pH 4.0) 50 µl and further incubated for one hour at 37° C. so that ammonia is removed from the glycosylamine and the oligosaccharides are released.

The obtained solution was then pyridylaminated (PA) using PALTSTATION® (Takara Bio Inc.) according to the manufacturer's protocol.

Figure 5:
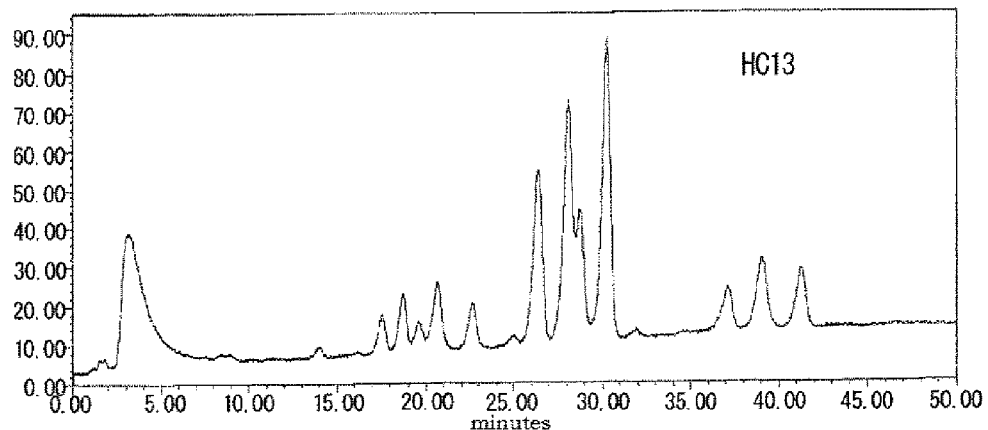
FIG. 5 Representative HPLC profile of IgG oligosaccharides derived from a healthy control.
Figure 6:
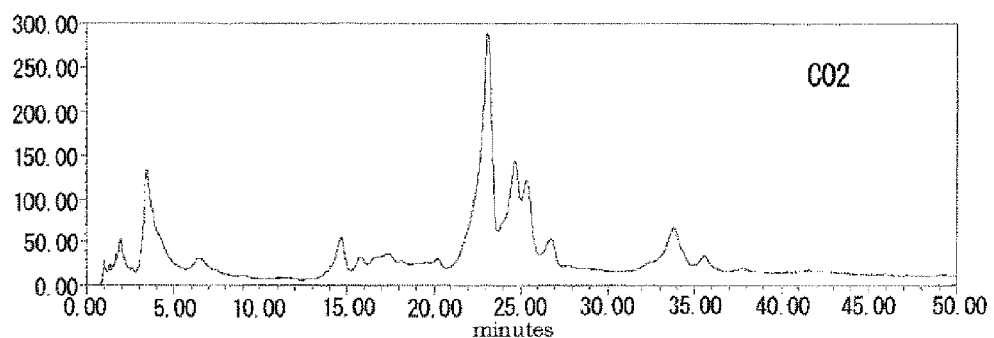
FIG. 6 Representative HPLC profile of IgG oligosaccharides derived from a patient with Crohn's disease.
Figure 7:
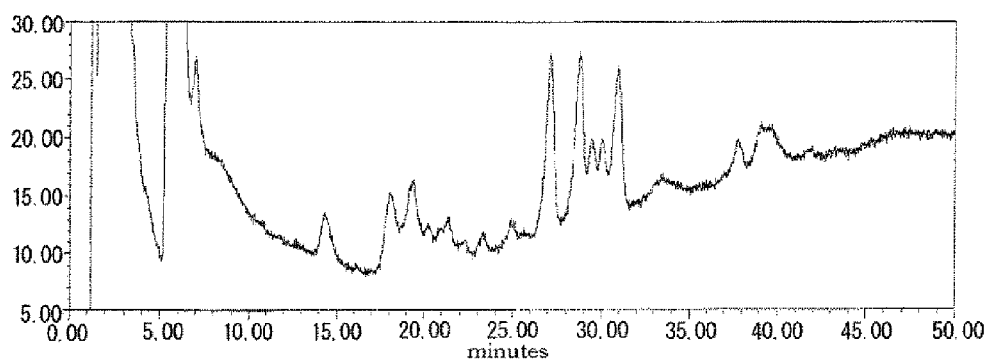
FIG. 7 Representative HPLC profile of IgG oligosaccharides derived from a patient with ulcerative colitis.

About 1/10 (about 200 pmol) of the PA-oligosaccharide was loaded onto an ODS silica column for oligosaccharides analysis PALPAK Type R (Takara Bio Inc.) equilibrated with a solvent containing 80% of solvent A and 20% of solvent B. The oligosaccharides were separated with a gradient of 20% to 50% solvent B for 50 minutes. PA-oligosaccharides were detected using a fluorescence detector (Ex. 320 nm, Em. 400 nm).
Column: PALPAK Type R (4.6 mmϕ×250 mm) Takara Bio Inc.
Solvent A: 10 mM acetic acid-trimethylamine (pH 3.8)
Solvent B: solvent A supplemented with 0.5% 1-butanol
Flow rate: 1.0 ml/min
Column temperature: 40° C.
Fluorescence Detector: Ex. 320 nm, Em. 400 nm Representative HPLC profiles obtained from a healthy control, a patient with Crohn's disease and a patient with ulcerative colitis are shown in FIGS. 5-7 respectively. The G0/G2 ratio was the ratio of the peak height corresponding to the G0 oligosaccharide represented by the above formula (I) or E in FIG. 2 to that corresponding to the G2 oligosaccharide represented by the above formula (II) or H in FIG. 2. Backgrounds of the patients were as follows:
FIG. 5:
Healthy control, Male, Age 58: G0/G2=0.57
FIG. 6:
Patient with Crohn's disease, Male, Age 17, colon type Crohn's disease: G0/G2=7.93
FIG. 7:
Patient with ulcerative colitis, Male, Age 17, pancolitis: G0/G2=1.21

Figure 8:
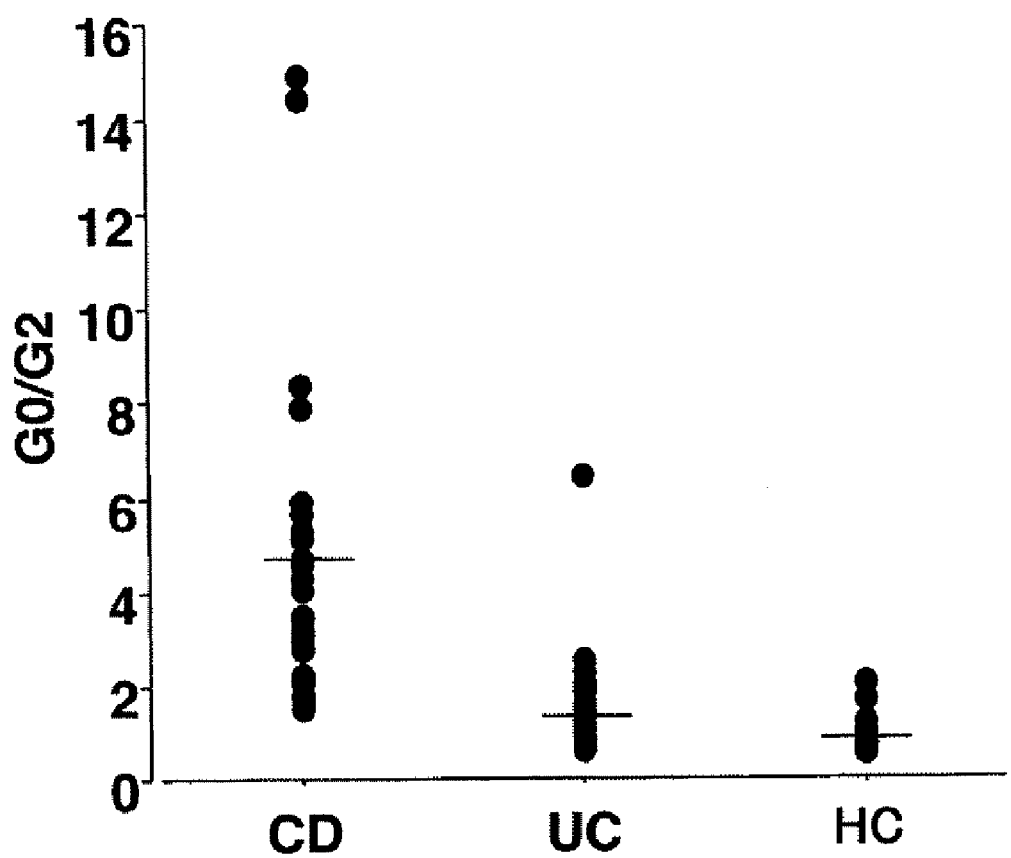
FIG. 8 Distributions of G0/G2 of patients with Crohn's disease (CD), with ulcerative colitis (UC) and healthy controls (HC).

In addition, distribution of G0/G2 of all cases is shown in FIG. 8. HPLC profiles were divided between the group of Crohn's disease, and the group of ulcerative colitis and healthy controls. In all patients with Crohn's disease, the peak corresponding to G0 oligosaccharide was higher than G2 oligosaccharide. Given the G0/G2 ratio equal to or higher than 2.1 was positive, all of the healthy controls were negative and 81% of the patients with Crohn's disease and 21% of the patients with ulcerative colitis were positive. Given the G0/G2 ratio equal to or higher than 1.5 was positive, all patients with Crohn's disease were positive and 37% of the patients with ulcerative colitis and 20% of healthy volunteers were positive. The correlation between number of the positive/negative people in each group and the given cutoff value (1.5, 2.0 and 2.1) is shown in Table 2.

TABLE 2

Correlation between G0/G2 cutoff value and positive rate:

| cutoff value | CD | UC | HC |
|---|---|---|---|
| >=2.1 | 22/27 (81%) | 3/27 (11%) | 0/10 (0%) |
| >=2.0 | 23/27 (85%) | 4/27 (15%) | 1/10 (10%) |
| >=1.5 | 27/27 (100%) | 10/27 (37%) | 2/10 (20%) |

Example 2

Similar test as Example 1 was conducted using serum obtained from 45 patients with Crohn's disease (CD), 42 patients with ulcerative colitis (UC) and 25 healthy volunteers (HC). Detailed patient characteristics are presented in Table 3.

TABLE 3

Patient Characteristics

|  | CD n = 45 | UC n = 42 | HC n = 25 |
|---|---|---|---|
| Male/Female | 35/10 | 26/16 | 15/10 |
| Age, yr, mean (SD) | 38.8(15.4) | 40.0(15.4) | 37.6(11.7) |
| Smokers, n (%) | 15(33) | 7(17) | 6(24) |
| Age at diagnosis, yr, mean (SD) | 28.9(13.7) | 35.0(15.2) |  |
| Bowel surgery (including appendectomy), n (%) | 30(67)* | 2(5) |  |
| Extraintestinal manifestations, n(%) | 4(9) | 2(5) |  |
| Treatment: | | | |
| Salazosulfapyridine or mesalazine, n (%) | 38(84) | 35(83) |  |
| Steroids, n (%) | 4(9) | 19(45)* |  |
| 6-MP/AZA, n (%) | 4(9) | 1(2) |  |
| Infiximab, n (%) | 4(9) | 0(0) |  |
| Antibiotics, n (%) | 5(11) | 2(5) |  |
| Total parental nutrition or elemental diet, n (%) | 29(64)* | 4(10) |  |
| No treatment, n (%) | 1(2) | 2(5) |  |
| Disease location(n) | | | |
| Small bowel/colon/both/unknown | 9/8/28 |  |  |
| Extensive/left colon/rectum and sigmoid |  | 24/10/8 |  |
| Disease behaviors (n): | | | |
| Inflammatory/structuring/penetrating/unknown | 13/20/12 |  |  |
| CRP(mg/dL), mean(SD) | 1.6(3.3) | 1.7(3.5) |  |
| CDAI, mean(SD) | 197(102) |  |  |
| CAI, mean(SD) |  | 5.7(5.7) |  |

*p < 0.001

Serum IgG was purified using Protein G column (Amersham Biotech, Bucks, UK). In detail, half-diluted serum with phosphate buffered saline (PBS) was loaded onto the Protein G column. The column was subsequently washed with a minimum of 10 column volumes of PBS, followed by the same volume of 10 mM ammonium bicarbonate. Column-bound IgG was eluted using 0.1% trifluoroacetic acid (pH 2.2). The concentration of IgG was measured using Nanodrop ND-1000 spectroscopy (Nanodrop Technologies, Wilmington, Del.) at 280 nm.

The purified IgG sample (10-20 nmol) was dried with SpeedVac system (Labconco Corp., Kansas City, Mo.) and then dissolved in 20 µl of 100 mM ammonium bicarbonate. N-linked oligosaccharides were released from purified IgG samples by overnight incubation with 0.5 mU Glycopeptidase F (Takara Bio Inc.) at 37° C. Oligosaccharides were further incubated with 50 mM ammonium acetate (pH 4.0) for 30 minutes and lyophilized.

The released oligosaccharides were labeled with 2-aminopyridine by GlycoTag (Takara Bio Inc.) following the manufacturer's instructions. Excess 2-aminopyridine was removed with a cellulose cartridge glycan preparation kit (Takara Bio Inc.) and then oligosaccharides were incubated with 2M acetic acid at 80° C. for 2 hours to remove sialic acids.

Pyridylamino-(PA-)oligosaccharides from IgG were analyzed on reverse phase HPLC system (Waters Corp., Milford, Mass.).

Column: PALPAK Type R-MB (2 mmφ×150 mm, Takara Bio Inc.)
Solvent A: 10 mM sodium phosphate buffer (pH 4.4)
Solvent B: sodium phosphate buffer supplemented with 0.5% 1-butanol
Flow rate: 0.5 ml/minute
Column temperature: 40° C.

The glycans were separated with a gradient of 0% to 50% solvent B for 30 minutes followed by 10 minutes of 50% solvent B. PA-oligosaccharides were detected using a fluorescence detector (Waters 2475) (Ex 320 nm, Em 400 nm).

Figure 9:
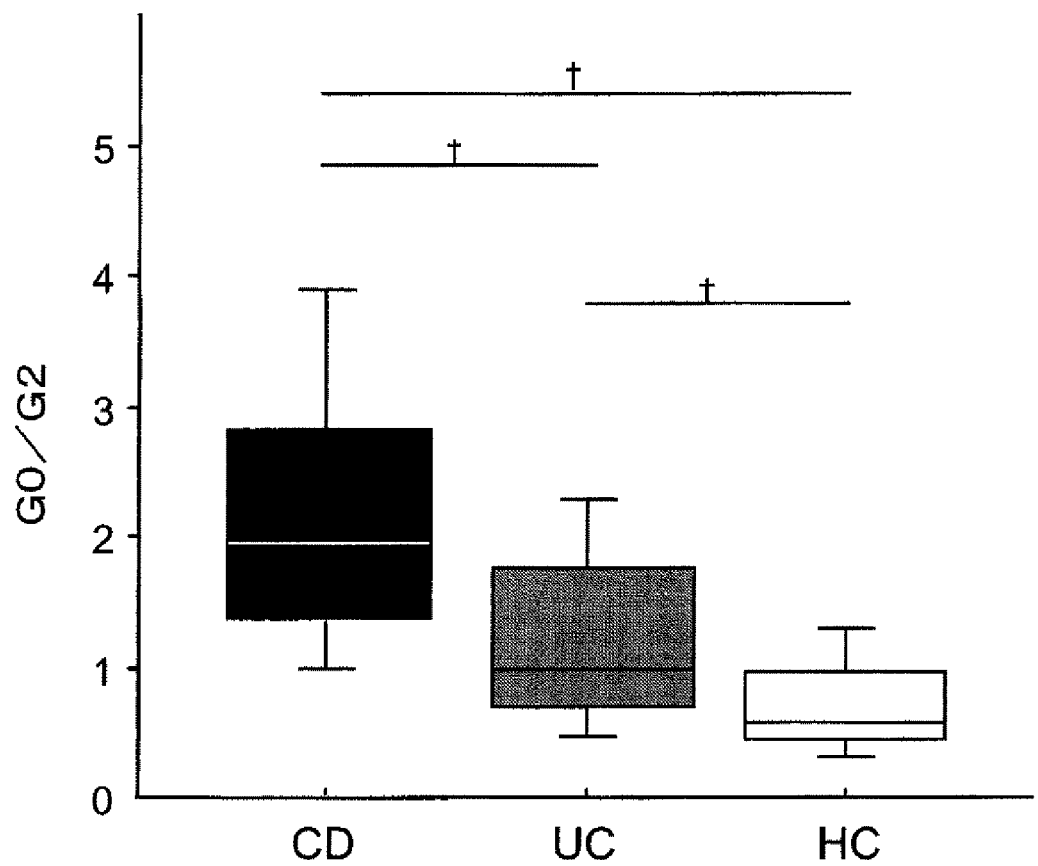
FIG. 9 Distributions of G0/G2 of patients with Crohn's disease (CD), with ulcerative colitis (UC) and healthy controls (HC).

G0/G2 of Crohn's disease patients and ulcerative colitis patients were higher than that of healthy volunteers. Crohn's disease (mean±SD): 2.33±1.58, ulcerative colitis: 1.24±0.78, and healthy volunteers: 0.69±0.34. See FIG. 9, (CD vs. HC: $p<0.01$, and UC vs. HC: $p<0.001$). In addition, G0/G2 of Crohn's disease patients was significantly higher than that of ulcerative colitis ($p<0.01$, FIG. 9).

Example 3

Figure 10:
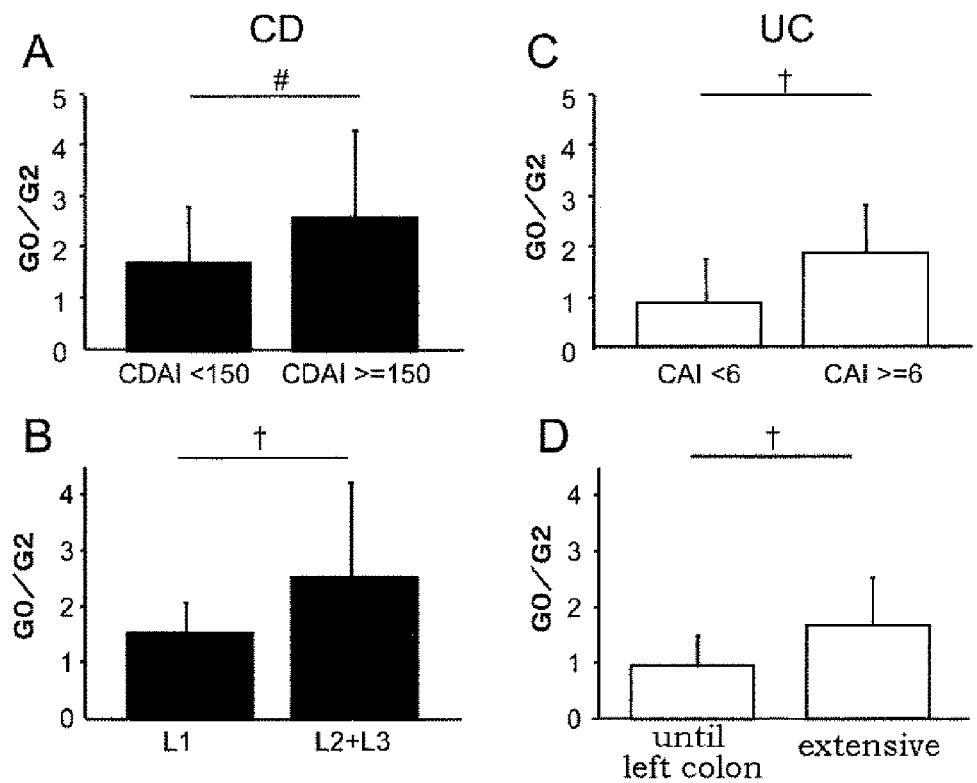
FIG. 10 Correlation between G0/G2 and clinical activities or lesioned area in patients with Crohn's disease (CD) and ulcerative colitis (US).

The inventors investigated whether or not G0/G2 correlates with clinical parameters. Clinical activities were determined using the Crohn's disease activity index (CDAI) for Crohn's disease or the clinical activity index (CAI) for ulcerative colitis. In Crohn's disease, G0/G2 in active patients (CDAI>=150) was significantly higher than that in patients in remission (CDAI<150; $P<0.01$, FIG. 10A). G0/G2 was also significantly higher in Crohn's disease patients with extensive disease where inflammation was not limited to the terminal ileum (Category L2 and L3 in Vienna Classification) than in patients with inflammation in the terminal ileum alone (Category L1; $P<0.05$, FIG. 10B). Similarly, G0/G2 was significantly higher in active ulcerative colitis patients (CAI>=6) than in patients in remission (CAI<6; $P<0.01$, FIG. 10C). G0/G2 was significantly higher in ulcerative colitis patients with extensive disease (total colitis) than in those with only left-side colon involvement ($P<0.05$, FIG. 10D). The inventors found no correlation between G0/G2 and the CRP level, age of onset, or disease duration (data not shown).

Example 4

The inventors investigated the effectiveness of agalactosyl IgG as a serologic marker for inflammatory bowel disease.

Figure 11A:
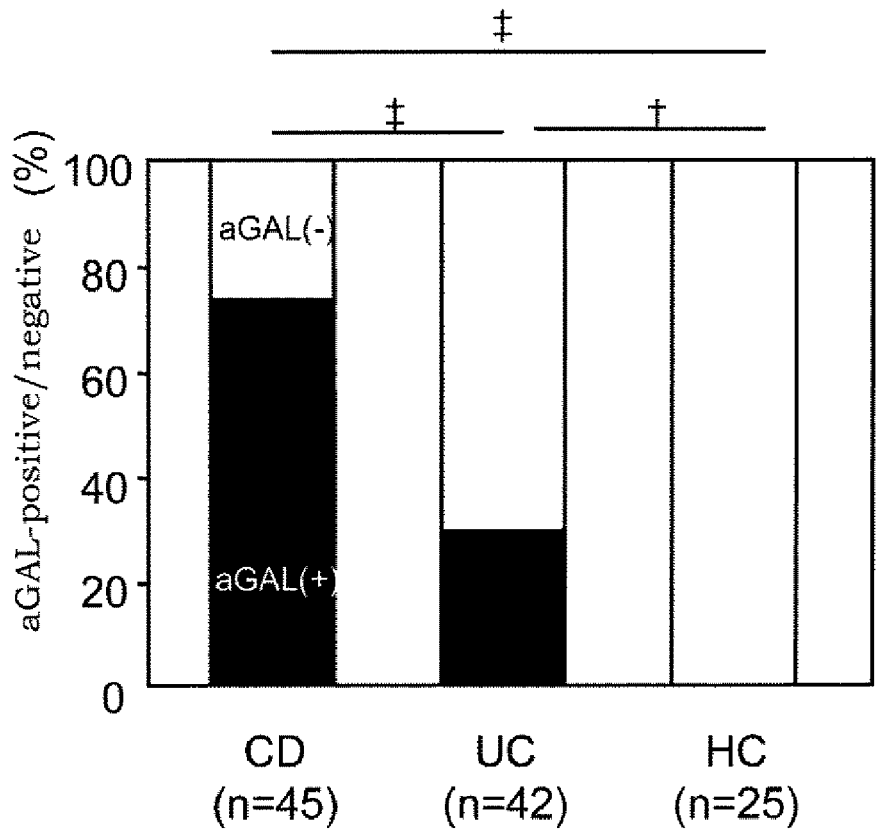
FIG. 11A Agalactosyl (aGAL) positive/negative rate in patients with Crohn's disease (CD) and ulcerative colitis (UC) as well as healthy controls (HC).

The condition in which G0/G2 was equal to or higher than 1.4, which was the mean±2SD of G0/G2 in healthy controls, was defined as positive in determining positive or negative of agalactosyl IgG (aGAL(+)/(−)). The positive rates in Crohn's disease, ulcerative colitis and healthy controls were 72%, 33% and 0%, respectively. The difference between each group was significant ($p<0.01$, FIG. 11A).

Figure 11B:
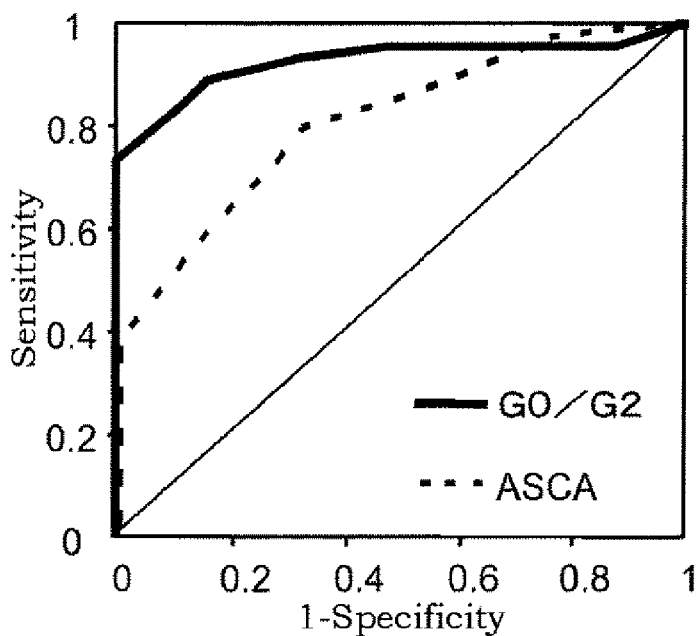
FIG. 11B The ROC curve for G0/G2 and ASCA levels for the discrimination between patients with Crohn's disease and healthy controls.
Figure 11C:
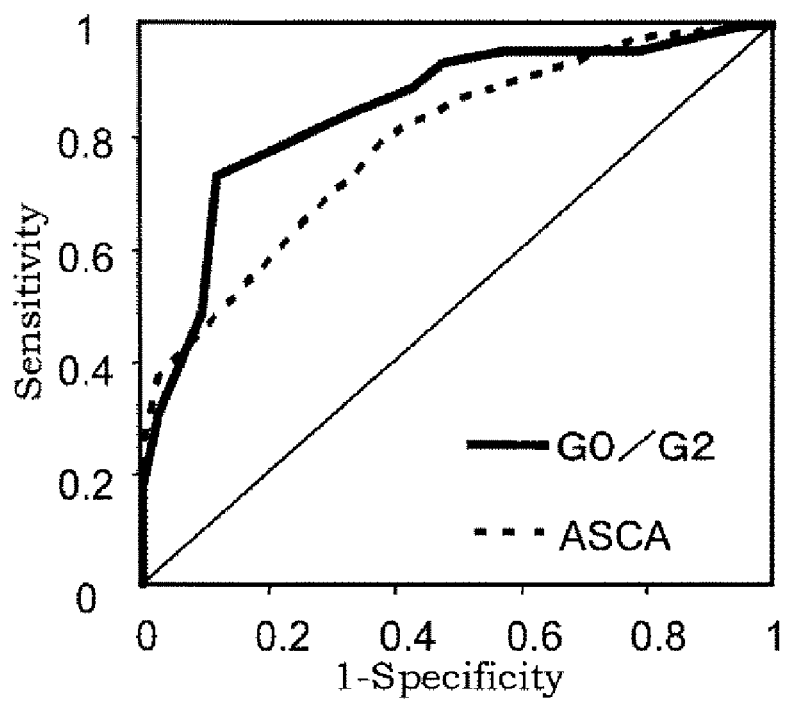
FIG. 11C The ROC curve for G0/G2 and ASCA levels for the discrimination between Crohn's disease and ulcerative colitis.
Figure 11D:
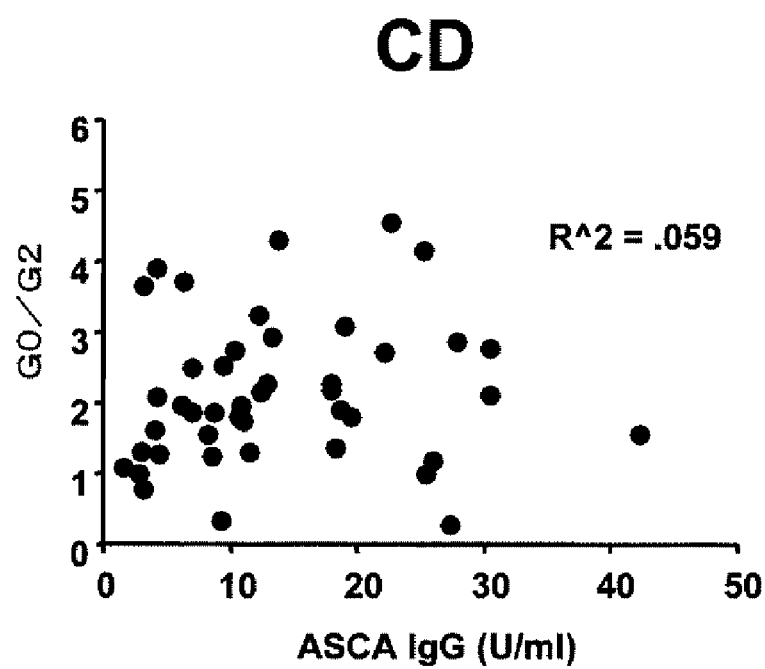
FIG. 11D The correlation between ASCA and G0/G2 in patients with Crohn's disease.
Figure 11E:
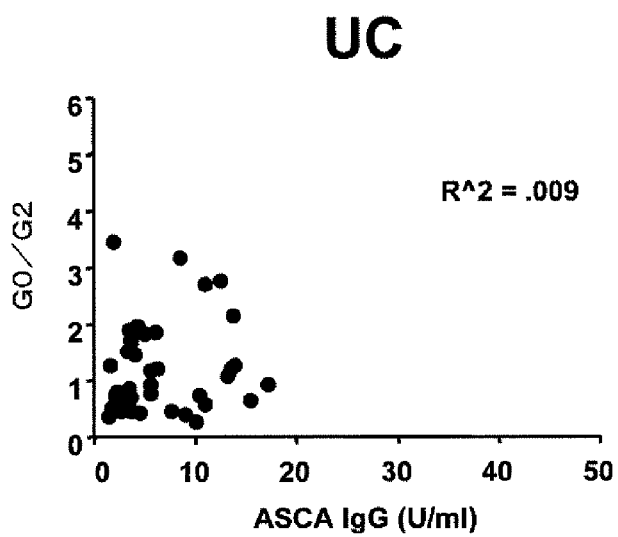
FIG. 11E The correlation between ASCA and G0/G2 in patients with ulcerative colitis.

The inventors then determined the level of anti-*Saccharomyces cerevisiae* antibody (ASCA) that has been known as most suitable marker for detecting Crohn's disease, and compared with G0/G2. Serum ASCA concentrations were examined using the ASCA IgG enzyme-linked immunosorbent assay kit (Genesis Diagnostics, Cambridge, UK) according to the manufacturer's instructions. Values over 10 U/ml were defined as positive. The sensitivity and specificity of G0/G2 were compared with ASCA for the discrimination of IBD by receiver operating characteristic (ROC) curve and area under the curve (AUC). Both the sensitivity and specificity of G0/G2 were higher than ASCA for the differentiation of Crohn's disease and healthy controls (AUC of G0/G2 vs ASCA=0.926 [95% confidence interval (CI), 0.872 to 0.980] vs 0.815 [95% CI, 0.732 to 0.897]; FIG. 11B). Moreover, both the sensitivity and specificity of G0/G2 were higher than those of ASCA for the differentiation of Crohn's disease and ulcerative colitis (AUC of G0/G2 vs ASCA=0.849 [95% CI, 0.780 to 0.918] vs 0.792 [95% CI, 0.714 to 0.869]; FIG. 11C). There was no correlation between G0/G2 and ASCA levels in Crohn's disease and ulcerative colitis (FIGS. 11D and 11E).

Example 5

The applicant then investigated the correlation between agalactosyl IgG (determined based on G0/G2) and prognosis of inflammation bowel disease. In this example, "clinical relapse-free" was defined as the condition in which patients maintain remission for more than 1 year by taking either salazosulfapyridine or 5-aminosalicylic acid (without corticosteroid, anti-tumor necrosis factor (TNF)-α antibody, and immunomodulators). Whether the agalactosyl IgG was positive or negative (aGAL(+)/(−)) was determined in the same manner as Example 4. The clinical relapse-free rate of aGAL(+) ulcerative colitis patients (11%) was significantly lower than that of aGAL(−) ulcerative colitis patients (77%; $P<0.001$, Table 4). The clinical relapse-free rate of aGAL(+) Chron's disease patients was lower than that of aGAL(−) patients (Table 4). Moreover, in ulcerative colitis patients whose CRP levels were negative at the time of blood sampling, the clinical relapse-free rate of aGAL(+) ulcerative colitis patients (0% (0/5)) was significantly lower than that of aGAL(−) ulcerative colitis patients (90% (19/21); $P<0.001$). Those results indicate the effectiveness of G0/G2 as a marker for prognosis in inflammatory bowel disease.

TABLE 4

Correlation between aGAL(+)/(−) and clinical relapse-free rate in CD and UC patients

|  | aGAL(−) | aGAL(+) | p value |
|---|---|---|---|
| CD | 50% (2/4) | 6% (1/17) | p = 0.08 |
| ALL UC | 77% (20/26) | 11% (1/9) | p < 0.001 |

Reference Example 1

IgG oligosaccharide profile in a patient with both ulcerative colitis and rheumatoid arthritis (RA) was investigated according to the same procedure as Example 1.

Figure 12:
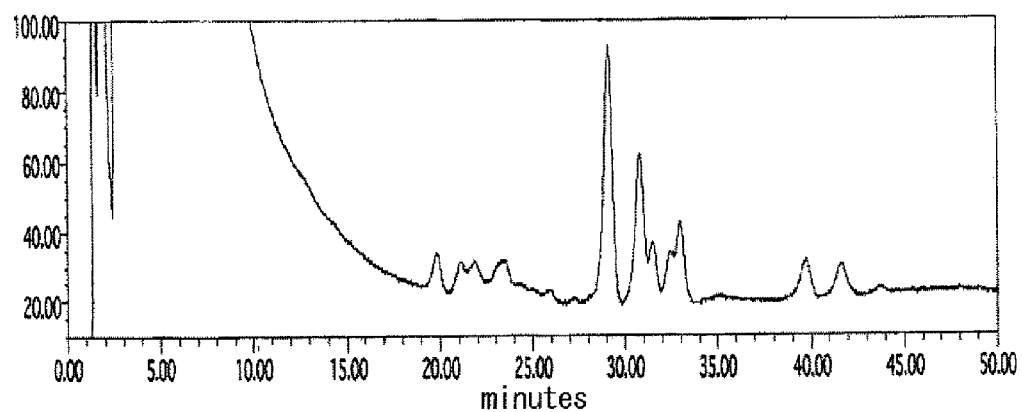
FIG. 12 Representative HPLC profile of IgG oligosaccharides from a patient with both rheumatoid arthritis and ulcerative colitis.

Patient with ulcerative colitis, female, age 69, CRP 5.43, left-side colon involvement, associated with RA. The HPLC profile of IgG oligosaccharides is shown in FIG. 12. The IgG oligosaccharide profile of this patient was similar to that of patients with Crohn's disease. G0/G2 was 2.70.

Example 6

The activity of β-galactosidase, which is responsible for the release of terminal galactose from IgG oligosaccharides in sera from patients with inflammatory bowel disease. Sera from patients with Crohn's disease and healthy controls were incubated with pyridylaminated biantennary oligosaccharides with an outer arm galactose (PA-sugar chain 001, Takara Bio, Inc.) for 3 days at 37° C. and these oligosaccharides were subjected to HPLC analysis. The terminal galactose was not depleted in the sera of patients with Crohn's disease or healthy controls, suggesting that there is no increase in β-galactosidase activities in the sera of either patient with Crohn's disease or healthy controls (data not shown).

The inventors next examined beta-galactosyltransferase enzyme activity of the patients with inflammatory bowel disease. Since IgGs are generated by plasma cells and B cells, the beta-galactosyltransferase (β4GalT) I mRNA expression in those cells were determined by means of real-time PCR procedure. In addition, the enzymatic activity of β4GalT I in plasma cells was examined.

Peripheral blood mononuclear cells (PSMC) were isolated from the venous blood of patients with inflammatory bowel disease or healthy controls by Ficoll-Hypaque density-gradient centrifugation. B cells and plasma cells were separated from PBMC with a B cell isolation kit II and plasma cell isolation kit, respectively (Miltenyi Biotech, Bergisch Gladbach, Germany), according to the manufacturer's instructions.

Total cellular RNA was isolated using Isogen-LS (Wako Chemicals, Osaka, Japan), and complementary DNAs were synthesized from the RNA using Superscript III first strand system (Invitrogen, Carlsbad, Calif., USA) according to the manufacturer's instructions. For TaqMan real-time reverse transcription-polymerase chain reaction (RT-PCR), the reaction mixture was prepared by TaqMan Universal PCR Master Mix with pre-designed and pre-labeled TaqMan PCR primer and probe set for human β-1,4-galactosyltransferase (β4GalT) I or human beta-actin endogenous control (Applied Biosystems, Foster City, Calif., USA). Real-time PCR was performed using an ABI PRISM 7900HT Sequence Detection System instrument and software (Applied Biosystems).

Isolated plasma cells were dissolved in TNE buffer (25 mM Tris-HCl (pH 7.8), 1% MP-40, 1 mM EDTA) 100 μl, sonicated, centrifuged at 12,000 G for 10 min. at 4° and the supernatant was collected. The cellular supernatant 7.5 μl was mixed with 80 mM UDP-galactose (Sigma-Aldrich, St. Louis, Mo.) 6.25 μl and 0.77 mM PA-agalactosyl N-linked oligosaccharides 5 μl, and the mixture was incubated and adjusted to 25 μl with HEPES buffer so that the final concentration of the acceptor molecule in the reaction mixture was 77 μM. The mixture was incubated at 37° C. for 24 hours and the reaction was terminated by boiling for 1 minute. The samples were then centrifuged at 12,000 g for 10 minutes and 5 μl of 25 μl supernatants were analyzed by HPLC as described above. β4GalT activity was calculated as follows; the area under the peak of galactosylated oligosaccharides was measured after the reaction and the concentration was determined using a standard galactosyl bi-antennary PA-oligosaccharide. β4GalT activity was expressed as nmol/hour by dividing the concentration of galactosyl oligosaccharides with the incubation time.

Figure 13A:
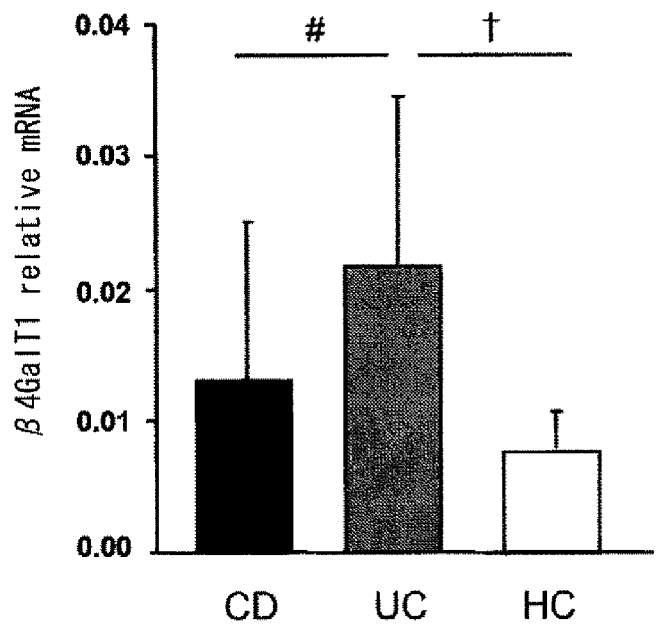
FIG. 13A Relative β4GalT I mRNA expression in plasma cells of patients with Crohn's disease (CD), ulcerative colitis (UC) and healthy controls (HC).
Figure 13B:
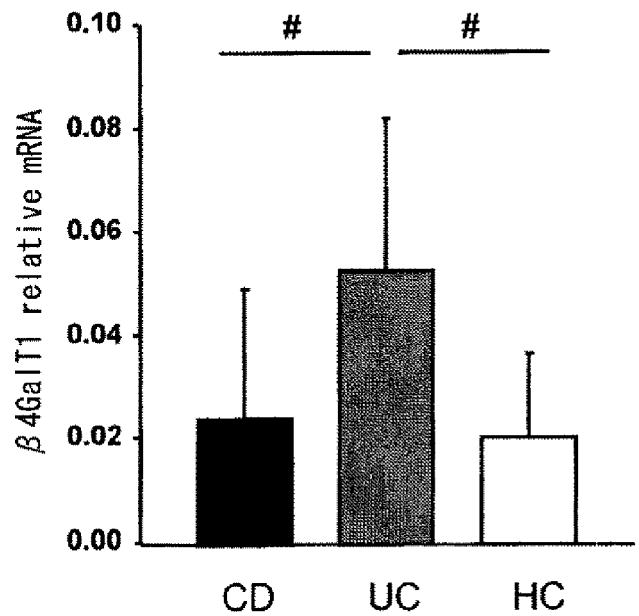
FIG. 13B Relative β4GalT I mRNA expression in B cells of the patients with Crohn's disease (CD), ulcerative colitis (UC) and healthy controls (HC).
Figure 13C:
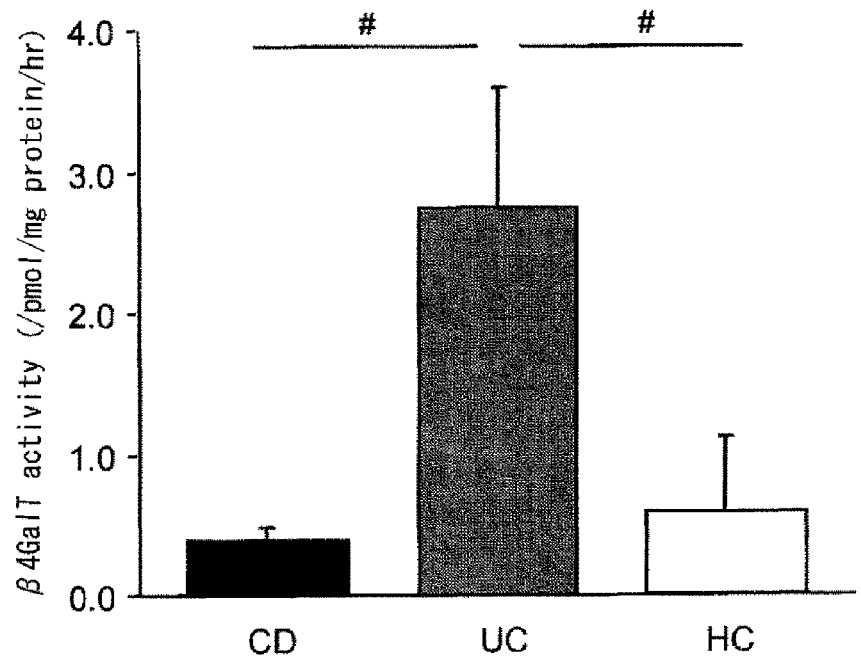
FIG. 13C Enzymatic activity of β4GalT I in plasma cells of patients with Crohn's disease (CD), ulcerative colitis (UC) and healthy controls (HC).

In plasma cells prepared from patients with ulcerative colitis, β4GalT I mRNA expression was significantly higher than that in patients with Crohn's disease (P<0.05) or healthy volunteers (P<0.01; FIG. 13A) β4GalT I mRNA expression in B cells of patients with ulcerative colitis was also significantly higher than that of patients with Crohn's disease or healthy volunteers (P<0.05; FIG. 13B). Furthermore, β4GalT activity in the plasma cells of patients with ulcerative colitis was higher than that of patients with Crohn's disease or healthy volunteers (FIG. 13C).

Reference Example 2

Figure 14:
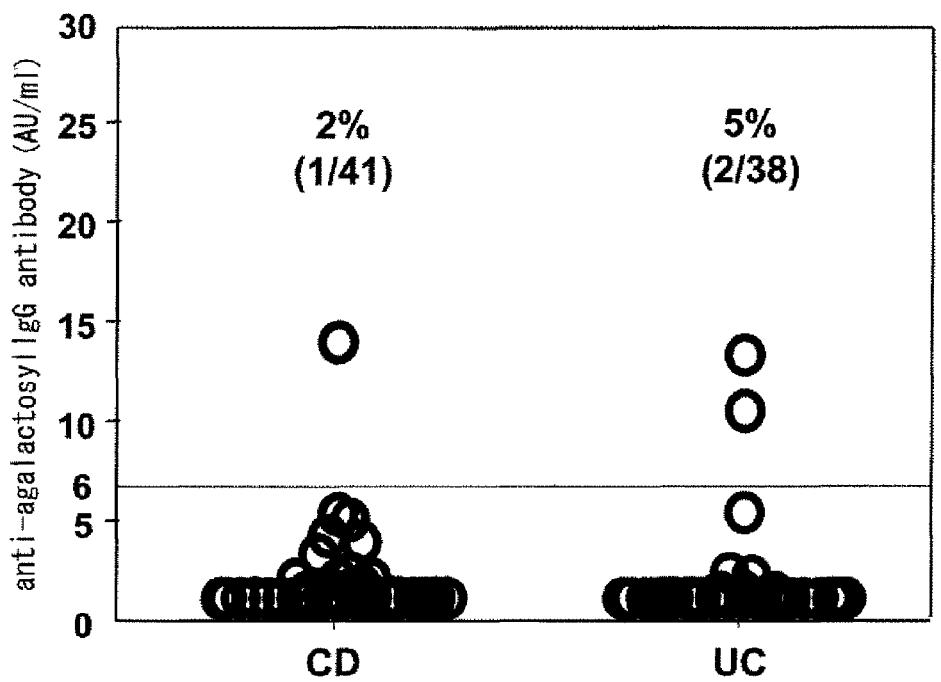
FIG. 14 Amount of serum anti-agalactosyl IgG antibody of patients with Crohn's disease (CD) and ulcerative colitis (UC).

Serum anti-agalactosyl IgG antibody, which has been used as a diagnostic marker for RA, was examined in patients with Crohn's disease and ulcerative colitis. Only 1 of 41 patients with Crohn's disease (2.0%) and 2 of 38 patients with ulcerative colitis (5%) were positive for anti-agalactosyl IgG antibody (FIG. 14). In these 3 patients that were positive for anti-agalactosyl IgG antibody, there were no differences in the disease characteristics or extraintestinal complications when compared with the patients negative for anti-agalactosyl IgG antibody.

This result suggests that anti-agalactosyl IgG antibody level is not suitable for differentiation diagnosis of inflammatory bowel disease, specifically, differentiation diagnosis between Crohn's disease and ulcerative colitis in a patient with inflammatory bowel disease.

The invention claimed is:

1. A method for the differential diagnosis of Crohn's disease or ulcerative colitis in patients having inflammatory bowel disease comprising, 1) isolating immunoglobulin G from the serum of a patient with Crohn's disease or ulcerative colitis,
2) releasing oligosaccharides from the immunoglobulin G,
3) determining the ratios of G0 oligosaccharide represented by formula (I):

to G2 oligosaccharide represented by formula (II):

to obtain G0/G2 ratios in the serum of the patient having Crohn's disease or ulcerative colitis and in the sera of healthy individuals,
wherein G represents galactose, M represents mannose, GN represents N-acetylglucosamine and F represents fucose in serum IgG oligosaccharide fraction, and
4) generating a relative ratio by comparing G0/G2 ratio in the serum of the patient having Crohn's disease or ulcerative colitis with G0/G2 ratios in the sera of healthy individuals, 5) comparing the relative ratio of step 4) to a predetermined value, wherein the predetermined value is obtained by comparing G0/G2 ratio in the sera of patients having Crohn's disease or ulcerative colitis with G0/G2 ratios in the sera of healthy individuals, and
6) differentially diagnosing the patient as having Crohn's disease when the ratio of G0/G2 is higher than the predetermined value, and the patient is diagnosed as having ulcerative colitis when the ratio of G0/G2 is lower than the predetermined value.

2. The method according to claim 1, in which the higher G0/G2 value means the higher severity of inflammatory bowel disease in the patient.

3. The method according to claim 1, in which the lower G0/G2 value means the better prognosis of the patient with inflammatory bowel disease.

* * * * *

UNITED STATES PATENT AND TRADEMARK OFFICE
CERTIFICATE OF CORRECTION

| | |
|---|---|
| PATENT NO. | : 8,043,832 B2 |
| APPLICATION NO. | : 12/301294 |
| DATED | : October 25, 2011 |
| INVENTOR(S) | : Eiji Miyoshi et al. |

It is certified that error appears in the above-identified patent and that said Letters Patent is hereby corrected as shown below:

On the cover of the patent, in the title (54), and col. 1, line 1, replace "METHOD FOR DETERMINATION OF INFLAMMATORY BOWEL DISEASE" with --METHOD FOR DIFFERENTIAL DIAGNOSIS OF INFLAMMATORY BOWEL DISEASE--.

Signed and Sealed this
Thirteenth Day of March, 2012

David J. Kappos
*Director of the United States Patent and Trademark Office*